United States Patent [19]

Paparizos et al.

[11] Patent Number: 4,786,756

[45] Date of Patent: Nov. 22, 1988

[54] CATALYTIC CONVERSION OF LACTIC ACID AND AMMONIUM LACTATE TO ACRYLIC ACID

[75] Inventors: Christos Paparizos, Willowick; Serge R. Dolhyj, Parma; Wilfrid G. Shaw, Lyndhurst, all of Ohio

[73] Assignee: The Standard Oil Company, Cleveland, Ohio

[21] Appl. No.: 668,045

[22] Filed: Nov. 5, 1984

[51] Int. Cl.$^4$ .................. C07C 51/377; C07C 57/065
[52] U.S. Cl. .................................... 562/599; 562/606; 568/484; 502/208
[58] Field of Search ...................... 562/599; 260/405.5

[56] References Cited

U.S. PATENT DOCUMENTS 2,174,830  10/1939  McAllister et al. .................. 562/599

Primary Examiner—Vivian Garner
Attorney, Agent, or Firm—C. S. Lynch; D. J. Untener; L. W. Evans

[57] ABSTRACT

Disclosed is a process for the catalytic conversion of lactic acid and/or ammonium lactate to acrylic acid by contacting a mixture of water and lactic acid and/or ammonium lactate in the vapor phase with aluminum phosphate which has been treated with an aqueous inorganic base.

5 Claims, No Drawings

CATALYTIC CONVERSION OF LACTIC ACID AND AMMONIUM LACTATE TO ACRYLIC ACID

This invention relates to a process for the catalytic conversion of lactic and/or ammonium lactate to acrylic acid by contacting the lactic acid or the ammonium lactate in the vapor phase with a treated aluminum phosphate, AlPO$_4$, catalyst.

Processes are being developed for the thermochemical conversion of biomass to lactate. For instance, sugars such as glucose, including sugars produced from acid hydrolysis of cellulosics are examples of such inexpensive starting materials. Development of such processes will provide an inexpensive source of lactic acid.

It is an object of the present invention to provide an improved process for the catalytic conversion of lactic acid or of ammonium lactate to acrylic acid. Other objects, as well as aspects, features and advantages, of the present invention will become apparent from a study of the accompanying disclosure and claims.

These objects are accomplished by the present invention according to which there is provided a process which comprises contacting an admixture of lactic acid and/or ammonium lactate and steam in the vapor phase with solid aluminum phosphate, AlPO$_4$, which has been treated with an aqueous inorganic base.

Although McAllister et al. in U.S. Pat. No. 2,174,830 disclosed the dehydration generally of hydroxy acids to the corresponding unsaturated organic acids using aluminum phosphate as a catalyst, the reaction is only applied to the dehydration of a carbonylic compound containing a carbinol group which yields an unsaturated carbonylic compound which forms an azeotrope having a higher ratio of water to unsaturated carbonylic compound than corresponds to the stoichiometric proportion for the dehydration reaction. Acrylic acid is not such a compound, and therefore the reference does not refer to the dehydration of the dehydration of lactic acid or of ammonium lactate.

According to the process of the present invention the lactic acid and/or ammonium lactate is contacted in the vapor phase while admixed with 0.1 to 50, usually 0.5 to 50, moles of steam per mole of lactic acid and/or ammonium lactate, with a solid aluminum phosphate catalyst that has been treated with an aqueous inorganic base, and calcined at a temperature in the range from 300° to 650° C., usually 450°-550° C. Calcination times are generally for a period of 10 minutes to 20 hours, usually 30 minutes to 10 hours. Calcination can be effected before or after the treatment with the base.

Such calcination usually is effected before using the catalyst in the conversion reaction of lactic acid or ammonium lactate to acrylic acid, but the calcination can take place at the beginning of the conversion run by contacting the solid, treated aluminum phosphate catalyst with the feed mixture of steam and lactic acid or steam and ammonium lactate. The pretreatment of the catalyst with an aqueous inorganic base increases the selectivity of the reaction to acrylic acid. Byproduct acetaldehyde is also desirable. The presence of water in the feed (in the form of steam) has also been found to increase the selectivity.

In the vapor phase reaction, it is also possible and often desirable to include nitrogen or recycle gas in the feed along with the steam and lactic acid or ammonium lactate. When such additional inert gas is used, it is usually used in an amount up to 30 moles per mole of lactic acid or ammonium lactate, usually up to 15 moles of nitrogen or recycle gas per mole of lactic acid or ammonium lactate. In other words, there can be 0 to 30 moles, usually 0 to 15 moles, of nitrogen, recycle or other inert diluent gas per mole of lactic acid and/or ammonium lactate feed.

The reaction of the invention is conducted in the temperature range from 250°-500° C., usually 320°-375° C., and at a contact time of 0.1-15, usually 2-4, seconds. When the reactant, or part of the reactant, is ammonium lactate, there is obtained, of course, lactic acid, plus ammonia.

The following examples are illustrative only and are not to be taken as limiting.

EXAMPLE 1

About 50 g. of AlPO$_4$ were heated in a muffle oven at 500° C. for 5 hours, after which the particulate aluminum phosphate was allowed to cool and then was pelletized and then broken up to a U.S. Sieve size of about 10-20 mesh. 20 cc of this catalyst was placed in a down flow tubular fixed bed reactor, heated to about 375° C. and treated for about 5 minutes with a nitrogen flow of 40 cc/min. measured at ambient conditions. The reactor and catalyst were cooled to 340° C. and while being held at this temperature a 14 weight percent NH$_3$ solution in water was fed into the top of the reactor by a syringe pump at a liquid flow rate of 0.1666 cc/min. for 30 minutes. Since the reactor was maintained at approximately atmospheric pressure, the ammonia and water of course immediately evaporated on entering the reactor.

After the ammonia treatment was terminated, lactic acid in water, together with nitrogen were fed into the top of the reactor, the mole ratio of lactic acid/water/nitrogen being 1/17.5/7.2. A high yield of acrylic acid and acetaldehyde were obtained and a low yield of propionic acid.

EXAMPLE 2

This example is exactly the same as Example 1, except for the different temperature and contact time as indicated in Table 1.

EXAMPLE 3

Example 1 was repeated exactly except that the feed was ammonium lactate instead of lactic acid.

EXAMPLES 4 AND 5

These examples are the same as Examples 1 and 2, respectively, except that the aluminum phosphate was not pretreated with any aqueous inorganic base before the conversion reaction. The lower yield of acrylic acid and the higher yield of propionic acid are both undesirable results when the base treatment is omitted.

EXAMPLE 6

In this example everything was the same as in Example 1, except that the catalyst was calcined at 600° C. instead of 500° C., and the reactor temperature was 375° C. instead of 340° C.

EXAMPLE 7

This example is exactly like Example 6 except that the conversion reactor temperature was 340° C.

EXAMPLE 8

20 g. of AlPO$_4$ were slowly added to a beaker containing 50 g. of a 5 percent potassium hydroxide solution. The suspension was filtered, and the filtercake was dumped to a ceramic dish and placed in a 110° C. oven and dried. Thereafter the dried material was calcined for 5 hours at 500° C. The particulate material was then pelleted and the pellets broken up to a 10–20 U.S. Sieve size. This catalyst was then used exactly as in Example 1, and the results are shown in Table 1.

EXAMPLE 9

This example was exactly the same as Example 8, except for the reactor temperature being 300° C. instead of 340° C. The results are shown in Table 1.

DEHYDRATION OF LACTIC ACID AND AMMONIUM LACTATE
20 cc FIXED BED PYREX REACTOR. FEEDS: SUBSTRATE/N$_2$/H$_2$O: 1.0/7.2/17.5

| Example No. | Temp. (°C.) | C.T. (sec) | Substrate Used | Percent Conversion | Acrylic Acid Yield, % | Propionic Acid Yield, % | Acetaldehyde Yield, % | CO Yield, % | CO$_2$ Yield, % |
|---|---|---|---|---|---|---|---|---|---|
| 1 | 340 | 4.2 | Lactic | 100 | 43.3 | 3.2 | 34.7 | 15.8 | 2.0 |
| 2 | 300 | 4.5 | Acid | 26.6 | 9.9 | 1.4 | 9.6 | 4.5 | .8 |
| 3 | 340 | 4.2 | Ammonium Lactate | 100 | 61.1 | 11.2 | 11.9 | 9.7 | 5.9 |
| 4 | 340 | 4.1 | Lactic | 97.7 | 20.6 | 23.4 | 22.7 | 24.8 | 5.6 |
| 5 | 300 | 4.3 | Acid | 75.9 | 8.8 | 21.1 | 21.0 | 20.2 | 4.2 |
| 6 | 375 | 4.0 | Lactic | 89.4 | 17.6 | 13.7 | 30.8 | 16 | 8.1 |
| 7 | 340 | 4.2 | Acid | 49.3 | 13.4 | 6.7 | 16.3 | 8.8 | 3.3 |
| 8 | 340 | 4.2 | Lactic | 98.1 | 32.1 | 15.0 | 17.5 | 20.3 | 8.0 |
| 9 | 300 | 4.6 | Acid | 24.6 | 8.9 | 3.1 | 2.2 | 8.5 | 1.1 |

% Yield = $\frac{\text{moles of carbon in a product}}{\text{moles of carbon in reactant}} \times 100$ As will be evident to those skilled in the art, various modifications of this invention can be made or followed in the light of the foregoing disclosure and discussion without departing from the spirit and scope of the disclosure or from the scope of the claims.

We claim:
1. A process for the catalytic conversion of lactic acid and/or ammonium lactate to acrylic acid which comprises contacting a mixture of water and lactic acid and/or ammonium lactate in the vapor phase with solid aluminum phosphate which has been treated with an aqueous inorganic base and calcined at a temperature in the range from 300° to 650° C.

2. A process of claim 1 wherein said base is aqueous ammonium hydroxide.

3. A process of claim 1 wherein said base is aqueous potassium hydroxide.

4. A process of claim 1 wherein said contacting is effected at a temperature in the range from 250°–450° C.

5. A process for the catalytic conversion of lactic acid and/or ammonium lactate to acrylic acid which comprises contacting a mixture of water and lactic acid and/or ammonium lactate in the vapor phase with solid aluminum phosphate which has been treated with an aqueous inorganic base and calcined at a temperature in the range from 320° to 375° C.

* * * * *